United States Patent
Martin

(10) Patent No.: US 10,240,779 B2
(45) Date of Patent: Mar. 26, 2019

(54) LOW NO$_x$ BURNER FOR ETHYLENE CRACKING FURNACES AND OTHER HEATING APPLICATIONS

(71) Applicant: Honeywell International Inc., Morris Plains, NJ (US)

(72) Inventor: Richard Ray Martin, Tulsa, OK (US)

(73) Assignee: Honeywell International Inc., Morris Plains, NJ (US)

(*) Notice: Subject to any disclaimer, the term of this patent is extended or adjusted under 35 U.S.C. 154(b) by 61 days.

(21) Appl. No.: 15/674,454

(22) Filed: Aug. 10, 2017

(65) Prior Publication Data

US 2017/0336068 A1 Nov. 23, 2017

Related U.S. Application Data

(62) Division of application No. 14/075,078, filed on Nov. 8, 2013.

(51) Int. Cl.
| | |
|---|---|
| *F23C 5/08* | (2006.01) |
| *F23D 14/06* | (2006.01) |
| *F23D 14/04* | (2006.01) |
| *F23D 14/64* | (2006.01) |
| *C07C 4/04* | (2006.01) |
| *F23D 14/10* | (2006.01) |
| *F23C 6/04* | (2006.01) |

(52) U.S. Cl.
CPC ............ *F23D 14/06* (2013.01); *C07C 4/04* (2013.01); *F23C 6/045* (2013.01); *F23D 14/04* (2013.01); *F23D 14/10* (2013.01); *F23D 14/64* (2013.01); *F23C 2201/20* (2013.01); *F23C 2900/06041* (2013.01)

(58) Field of Classification Search
CPC .......... F23D 14/22; F23D 14/06; F23D 14/02; F23D 14/12; F23D 14/10; F23D 14/105; F23D 14/145; F23D 14/125; F23M 5/025; F23C 6/047; F23C 6/045; F23C 6/042
See application file for complete search history.

*Primary Examiner* — Jason Lau

(57) ABSTRACT

A burner assembly for and method of producing ethylene having a mechanism to inject either primary fuel, staged fuel, or both by premix methods before combustion in a furnace. The burner assembly has at least one premix injection assembly for either exclusively primary fuel or exclusively staged fuel injection paired with a nozzle mix injection or injection means for primary and staged fuel both by premix methods. The primary fuel premix assembly associates with a burner tile that consists of multiple inlets and outlets connected by venturi channels to direct and combine combustion air and staged fuel coming from staged fuel orifice spuds. Primary fuel and combustion air are mixed in a premix assembly and directed inside the furnace, and above the burner tile to complete the reaction with the staged fuel and combustion air mixture in a combustion zone inside of the furnace.

11 Claims, 6 Drawing Sheets

LOW NO$_x$ BURNER FOR ETHYLENE CRACKING FURNACES AND OTHER HEATING APPLICATIONS

CROSS-REFERENCE TO RELATED APPLICATION

This application is a Division of copending application Ser. No. 14/075,078 filed Nov. 8, 2013, the contents of which cited application are hereby incorporated by reference in its entirety.

FIELD OF THE INVENTION

This invention relates generally to a burner assembly for use in a furnace. More specifically, the invention relates to a burner assembly for improved, ultra-low NO$_x$ burner performance in ethylene cracking furnaces.

BACKGROUND AND DESCRIPTION OF THE RELATED ART

Ethylene production continues to grow and has replaced acetylene for many applications. Ethylene production occurs mainly through pyrolysis which is the thermal cracking of various hydrocarbon streams in the presence of steam. The heat transfer in the radiant section of a thermal cracking furnace is critical. Cracking furnaces present both burner design and operating challenges in comparison to typical process heaters. The thermal cracking of hydrocarbons in the radiant section process tubes of a cracking furnace occurs at a higher temperature compared to most other refinery or chemical processes. In order to crack hydrocarbons in the presence of steam, the temperature of the combustion products in the radiant section of the furnace must be high to achieve the required heat transfer.

Fuel gas burned at high temperatures in an excess air environment results in the production of Nitrogen Oxides (NO$_x$). NO$_x$ is considered hazardous to the environment and, thus, environmental regulations have been placed on the quantity of NO$_x$ that could be produced in the combustion process in fired heaters and furnaces. Due to various regulations, burner designs used in cracking furnaces have evolved in recent years, improving the efficiency of combustion while reducing the amount of NO$_x$ produced. In one approach, staged combustion has been used to reduce the amount of NO$_x$ formed in the combustion process by reducing the flame temperature and reducing the concentration of oxygen available. Staged combustion involves delaying the mixing of the fuel and air and promotes the mixing of combustion products with the fuel and air mixture to provide a reduction in flame temperature and a reduction in the partial pressure of oxygen. Combustion products are the products of combustion from the burner which fill the inside of the furnace prior to discharge at the top of the furnace. Combustion products may be comprised of components such as carbon dioxide, water vapor, nitrogen and oxygen.

Historically, thermal cracking furnaces were fired with a large number of premix radiant wall burners. Premix radiant wall burners are well known for their short, compact flame, which can produce uniform heat flux throughout the radiant section of the furnace. Although premix burners are a common design in cracking furnaces there are significant cost issues associated with the use of premix burners because a large number of burners must be installed.

Current low NO$_x$ burner designs employed in cracking furnaces are typically nozzle mix "deeply" staged fuel configurations. Low NO$_x$ cracking furnace burners discharge fuel from two distinct locations. Typically one discharge location is in the burner tile throat area. This location discharges an initial source of fuel, called primary fuel, which comprises 10%-20% of the total fuel burned. The burners typically include one or more primary fuel nozzle mix tips that are located in a burner air passage that pass through the throat of a burner tile. This primary fuel burns in an environment with high excess air, which could lead to increased NO$_x$ formation if the fuel and air are not completely mixed. The remainder of the fuel needed for the process is injected at a secondary location which is external to the burner tile and downstream from an air passage discharge used to discharge the primary fuel. The fuel discharged at the second location is called secondary or staged fuel. Secondary fuel is normally discharged through multiple nozzle fuel tips that are located external of the burner tile. Such burner assemblies are normally referred to as "deeply" staged because they use two locations for the discharge of fuel and the majority of the fuel they utilize is staged at the secondary or staged location. For minimal NO$_x$ emissions, "deeply" staged fuel burners mix combustion products with the staged fuel prior to combustion in the secondary combustion zone. In such a design, the staged tip configurations that are necessary to minimize flame length and stabilize the flame in the secondary combustion zone entrain an insufficient amount of combustion products that are mixed with the staged fuel. Subsequently, the burner does not achieve maximum reduction in NO$_x$ emissions. These burners are either floor fired burners (hearth burners) or floor fired burners in combination with side wall or balcony burners. These burners employ a rectangular discharge opening of the burner tile that sits against the furnace wall and provides a flat flame. The low NO$_x$ premix assembly of the present invention incorporates staged fuel combustion and combustion product recirculation to reduce the level of NO$_x$ generated, while providing minimum flame length and maximum stability.

Recently, there has been an effort to reduce the physical size of the thermal cracking furnace which consequently reduces the furnace volume while increasing the heat density. Subsequently, by decreasing the length of the furnace, the space between burners has been reduced causing flame overlap and interference. This flame overlapping tends to cause NO$_x$ emissions to increase. Further, another effect of flame overlap is for the flame length to increase, so much so that the flames between the burners tend to protrude further into the furnace space between the furnace wall and the process tubes. Combustion product flow patterns in the radiant section of the furnace have a significant impact on the burner flame pattern. Combustion products flow upwards along a hot firing wall, while a downward flow recirculates back toward the furnace floor along the surface of the lower temperature tubes. If the burner flames become too long then the combustion product flow within the furnace is able to draw the flames across the furnace to the tubes causing overheating of the tubes which may lead to tube failure.

Additionally, prior art burner designs have further complications. The nozzle mix "deeply" staged fuel burner configuration results in a low discharge velocity as the primary fuel combustion products and any excess combustion air exits the burner tile. Also the prior burner design results in a delayed mixing of combustion air with the deeply staged fuel. Therefore, with the combination of circulation patterns in the furnace, low discharge velocity, and the delayed mixing of combustion air and staged fuel, a complication called "flame rollover" commonly results. Flame rollover can occur in the upper portions of the flame resulting in flame impingement or hot gas impingement on the process tubes.

Yet another complication of the "deeply" staged fuel configurations is that the delayed burning of the staged fuel creates a relatively low combustion temperature above the top of the burner tile and therefore the desired radiant flux profile may not be available for appropriate heat transfer giving a lower than desired efficiency.

Accordingly, it is therefore desirable to provide a cracking furnace burner assembly with a burner tile design that allows for an efficient mechanism to mix combustion products with the air and fuel within the burner tile prior to combustion in the furnace thereby providing an extremely uniform high velocity mixture that reduces the flame length as well as subsequent complications such as flame rollover.

It is further desirable to provide a cracking furnace burner assembly that uses premix methods for discharging either or both primary and staged fuel providing a uniform fuel, air and combustion product-mixture prior to combustion thereby minimizing $NO_x$ emissions and flame length.

It is yet further desirable to provide a burner assembly design that uses premix fuel burner tips that allow gas mixtures to exit the burner tile at an extremely high velocity to prevent flame rollover.

It is yet further desirable to provide a burner assembly design that utilizes combustion products from within the furnace in order to cool the system, thereby minimizing $NO_x$ levels.

It is yet further desirable to provide a burner assembly design that allows for the complete mixing of the primary fuel and the air promoting the initial 50% of combustion to occur close to the tile discharge of the burner tile and under sub-stoichiometric conditions.

It is yet further desirable to provide a burner assembly design that eliminates delayed combustion accounted for in deeply staged fuel designs.

SUMMARY OF THE INVENTION

In general, in a first aspect, the invention relates to a low $NO_x$ burner assembly for use in an ethylene cracking furnace or similar heating application.

The burner assembly may provide for a flat flame shape or a round flame shape. The burner assembly uses premix methods of discharging fuel through a choice of discharge locations. Therefore, one embodiment of the assembly provides an improvement to discharge primary fuel while retaining the current method of discharging staged fuel, another embodiment of the assembly provides an improvement upon the method of discharging staged fuel while retaining the current means of discharging primary fuel, and yet another embodiment of the assembly provides improvement for discharging both the primary fuel and the staged fuel.

In the preferred embodiments, a portion (approximately 50%) of the fuel is delivered directly to the primary mixer tips while the remaining portion of the fuel is delivered to the staged fuel spuds. The primary premix venturi and tip assemblies are designed such that most (approximately 90%) of the stoichiometric air required for combusting the primary fuel is induced into the primary combustion zone by the primary fuel. The fuel and air mixture that exits a primary venturi and tip assembly is a very uniform fuel rich mixture that burns under sub-stoichiometric conditions resulting in a low generation of NOR. The uniform mixture permits the combustion of the fuel without any transition from an air rich condition to a fuel rich condition that occurs during the mixing of the two streams in a nozzle mix burner. The excess air combustion that occurs during this transition creates high $NO_x$ emissions.

The remainder of the required combustion air enters the burner tile through multiple combustion air inlets that are cast into the tile. Venturi channels are also cast into the burner tile. Multiple staged fuel spuds are located at the inlet of these venturi channels in the lower portion of the tile. The energy from the staged fuel entrains combustion products from the furnace resulting in the mixing of the combustion products and staged fuel with the combustion air before exiting the tile and entering into the burner combustion zone. The combustion of this mixture of fuel, combustion products, and combustion air generates extremely low $NO_x$ levels.

The mixture of combustion products, staged fuel and combustion air is injected at a slight angle towards the primary fuel and air mixture above the burner tile providing the additional combustion air required for complete combustion of the primary fuel.

Figure 1:
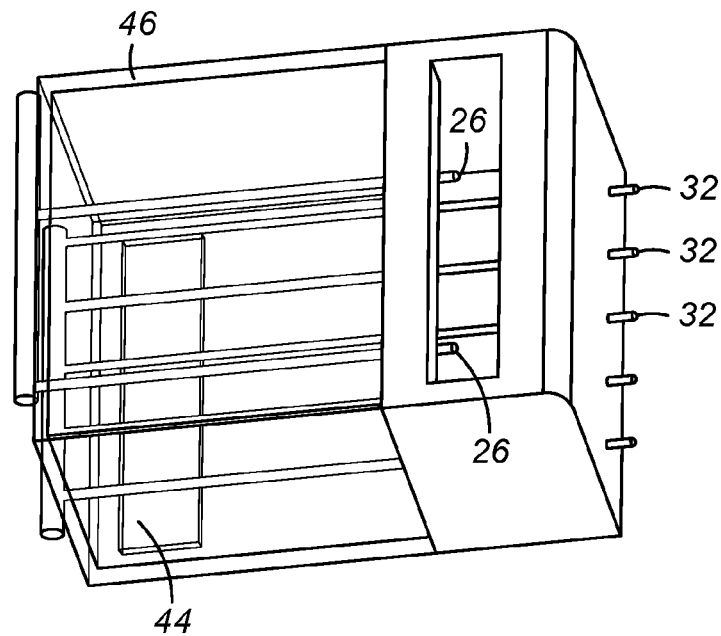
FIG. 1 is a perspective view of a prior art burner design currently used in Low $NO_x$ cracking furnaces.

Other advantages and features will be apparent from the following description, and from the claims.

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

As shown in the drawings and understood by those skilled in the art, the burner assembly may be associated with a furnace or other heating applications to generate heat in a petroleum refinery, petro-chemical plant, or other applications.

Referring now to FIG. 1, a perspective view of a prior art burner design currently used in low $NO_x$ cracking furnaces. The current state-of-the-art low $NO_x$ cracking furnace burner designs have a primary fuel discharge and a secondary fuel discharge. As shown in FIG. 1, current burners in the art employ a nozzle mix tip design for both the primary fuel tips 26 and the staged fuel tips 32. Nozzle mix tips are ordinary tips that do not provide for a method of mixing fuel with combustion air before discharge of the fuel into the combustion zone. The primary fuel discharge of a prior art burner is in the throat of the burner tile. The primary fuel tips 26 are in the combustion air flow passage. Combustion air comes from outside of the furnace through a windbox opening 44 and into the windbox 46. Two primary fuel tips 26 are shown, however the number may vary. In such a prior art burner design, the secondary or staged fuel is discharged near the base of the burner tile. As shown, the staged fuel tips 32 of prior art designs are external to the burner tile so that the staged fuel would discharge upward along the outer surface of the burner tile. Because the prior art designs use nozzle mix tips to discharge fuel, both the primary fuel and the secondary fuel exit first into a combustion zone prior to mixing with any combustion air.

Figure 2:
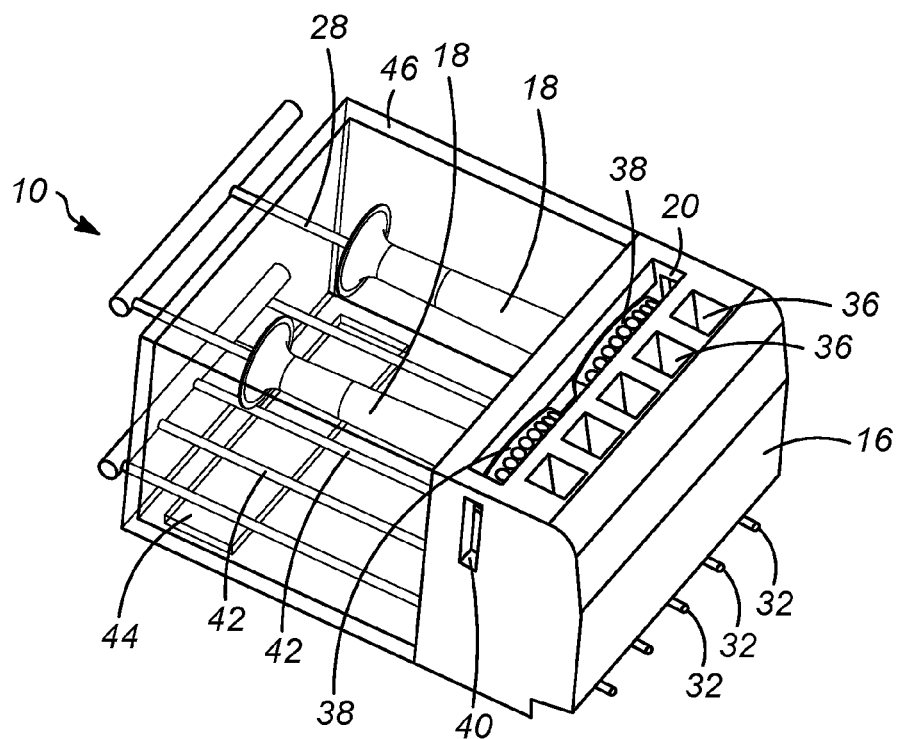
FIG. 2 is a perspective view of a first preferred embodiment of a burner assembly constructed according to the present invention.
Figure 3:
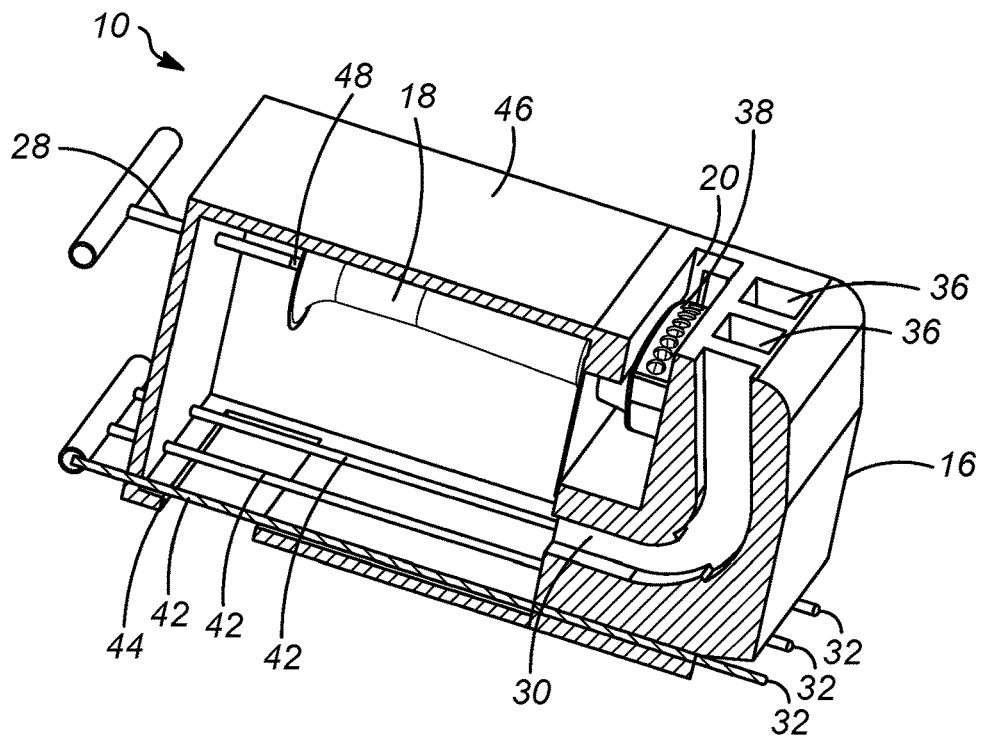
FIG. 3 is a cross sectional view of a first preferred embodiment of a burner assembly constructed according to the present invention.

FIGS. 2 and 3 show a first preferred embodiment of the present disclosure. FIG. 2 is a perspective view of a first preferred embodiment of a burner assembly. In the first preferred embodiment of the burner assembly, the primary fuel is mixed with combustion air prior to being discharged into a combustion zone within the furnace. Then this improved primary premix fuel discharge method of this preferred embodiment can be used with the current state-of-the-art nozzle mix or raw gas tip method to inject secondary or staged fuel.

The burner assembly 10 includes a burner tile 16. The burner tile 16 may be rectangular in shape with six sides. The burner tile 16 sits within the furnace and serves to house and associate different components of the burner assembly 10. The burner tile 16 has a front side that is parallel and adjacent to the furnace wall 12. The remaining five sides of the burner tile 16 are positioned so that they sit or reside within the furnace. The remaining sides include a top side, a bottom side, a back side, and two sides that sit directly opposite one another. A windbox 46 extends away from the burner tile 16 and furnace. The windbox 46 has an opening 44 for the entrance of combustion air. The burner tile 16 may include a rectangular discharge opening 20 on the top side of the burner tile which may produce a rectangular, flat flame that lies against the furnace wall (not shown) which provides uniform heat distribution along the furnace wall 12. Although not shown in the drawings, the burner tile configuration may also be rounded per requirement by each particular burner application.

As best illustrated in FIG. 3, a portion of fuel, referred to herein as primary fuel, enters at high pressures through at least one primary fuel riser 28 that direct primary fuel into a primary fuel orifice spud 48. The primary fuel orifice spud 48 introduces the primary fuel into the premix venturi and tip assembly 18 which is fluidly connected to a primary fuel riser 28. The primary fuel may be natural gas fuel or any other gaseous fuels typically used in fired industrial applications. The premix venturi and tip assembly 18 may connect to the burner tile 16 and may extend outwardly away from the burner tile 16. The premix venturi and tip assembly 18 connects to the burner tile 16 by a connective opening so they are in fluid communication.

Figure 9:
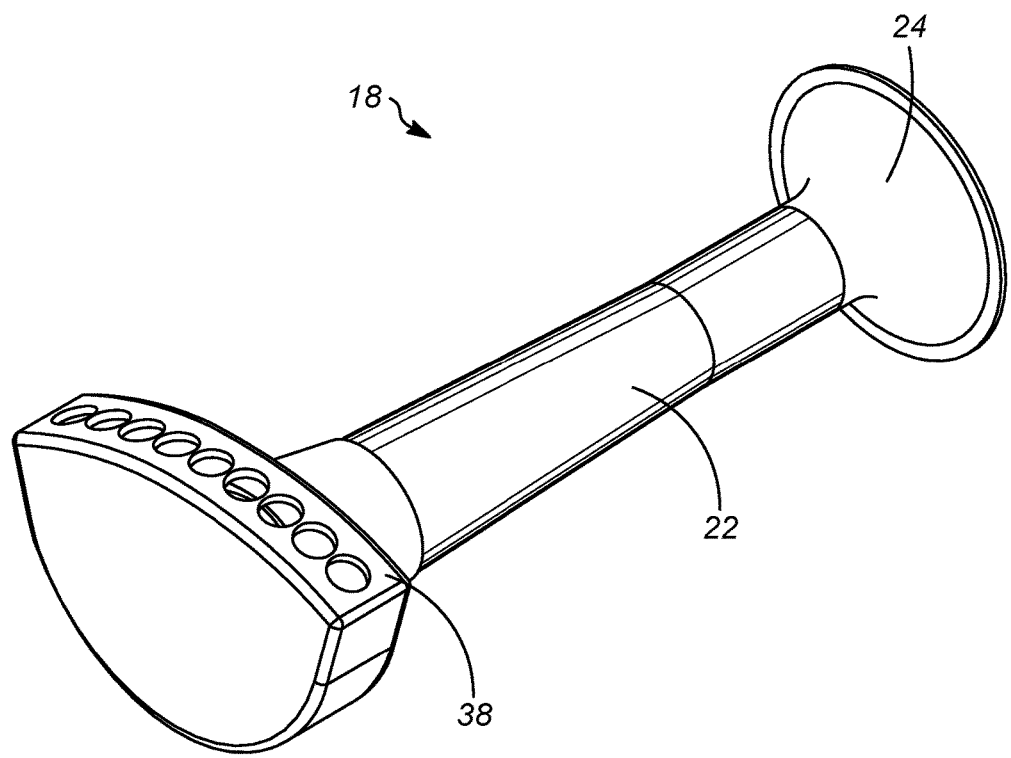
FIG. 9 is a perspective view of a premix primary venturi and tip assembly constructed according to the present invention.

Shown in more detail in FIG. 9, the premix venturi and tip assembly 18 consists of an inlet 24 which is in fluid communication with an elongated venturi mixing chamber 22. The primary fuel riser 28 introduces the primary fuel into the premix venturi and tip assembly 18 by way of a primary fuel orifice spud 48. The admittance of primary fuel into the venturi mixing chamber 22 induces combustion air into the venturi mixing chamber 22. The combustion air is drawn in from outside of the furnace through a windbox opening 44. The premix venturi and tip assembly 18 is designed such that approximately ninety percent (90%) of the stoichiometric air required for combusting the primary fuel is induced into the burner assembly by the primary fuel. The primary fuel and combustion air create a mixture within the premix venturi and tip assembly 18. The primary fuel and combustion air mixture discharges through the primary mixer tip 38 which is in fluid communication with the premix venturi and tip assembly 18. The primary mixer tip 38 sits within the burner tile 16 and is associated with the discharge opening 20 to discharge the pre-mixed primary fuel and combustion air mixture above the burner tile and into the combustion zone of the furnace space. The primary fuel and combustion air mixture that exits the primary mixer tip 38 is a uniform mixture that burns under sub-stoichiometric conditions resulting in low levels of $NO_x$ generation. The uniformity of the mixture is important to ensure conditions that have little to no excess oxygen or air. The mixture of the fuel and air burns rapidly providing a well-defined, compact flame that is desirable to achieve the required heat flux to the process tubes. Further, the combustion of the uniform mixture occurs close to the discharge 20 of the burner tile 16 thereby eliminating a problem of deeply staged fuel designs and the relatively low combustion temperature above the top of the burner tile. The fuel and combustion air mixture exits the primary mixer tip 38 at an extremely high velocity. As a result, the high velocity of the primary fuel and combustion air mixture combines with the combustion products in the furnace and adheres to the hot firing wall of the furnace until the mixture reaches the top of the furnace. Inside the furnace space of the furnace, the burner flames tend to flow upward and vertically, also adhering along a hot firing wall while combustion products flow or recirculate along the opposite wall of the furnace where the process tubes are located. Due to the high velocity of the mixture relative to the current inside the furnace the flame is not pulled away from the furnace wall by the low velocity furnace currents. Therefore, the flame does not rollover and contact the tubes. Shown in FIG. 2, the burner tile 16 may have a passageway 40 on either side of the burner tile 16 to allow the high velocity primary fuel and combustion air mixture to circulate combustion products from inside of the furnace into the burner tile 16 in order to further reduce flame temperature and subsequently reduce the amount of $NO_x$ generated by the combustion of the primary fuel.

In this embodiment, secondary or staged fuel is injected through staged fuel risers 42 and discharges through staged fuel tips 32 by way of the nozzle mix tip method that is currently used in prior art. The staged fuel tips 32 are positioned external to the burner tile 16 similarly to that in prior art burner assemblies. After injection, the staged fuel travels upward along the outer face of the burner tile 16 and does not mix with combustion air until it reaches the combustion zone in the furnace space which is above the burner tile 16. Combustion air enters from outside of the furnace and into windbox 46 through windbox opening 44. The combustion air may then enter the burner tile 16 through a single secondary combustion air slot (not shown) or multiple secondary air inlets 30 that are cast into the burner tile 16 and communicate from the air inlet to the furnace space. The secondary combustion air exits the burner tile 16 through discharge outlets 36 into the burner combustion zone of the furnace where it meets with the staged fuel traveling from the exterior of the burner tile 16.

Figure 4:
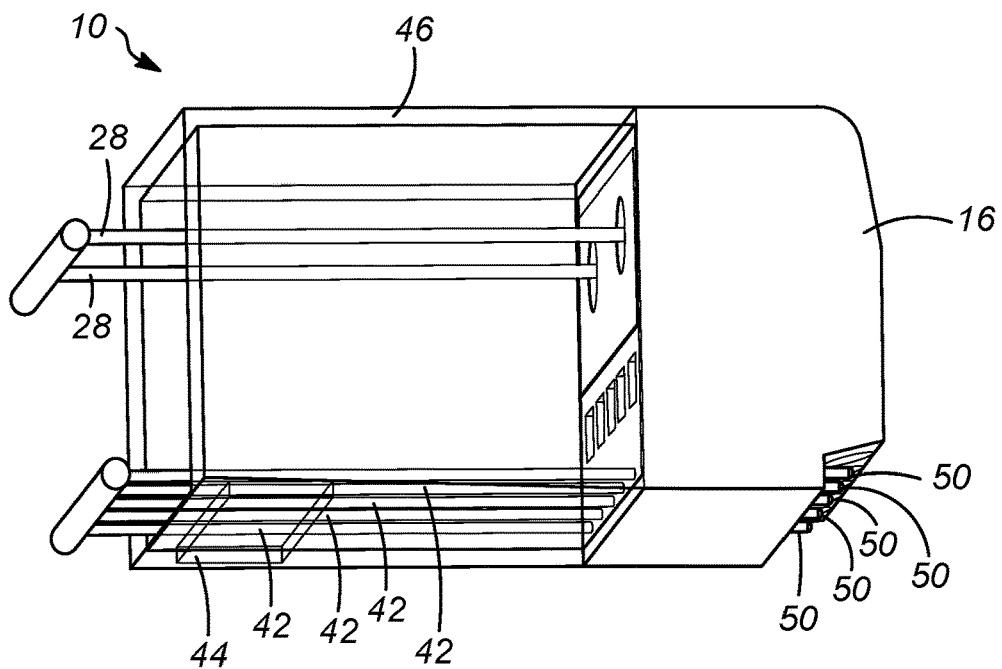
FIG. 4 is a perspective view of a second preferred embodiment of a burner assembly constructed according to the present invention.
Figure 5:
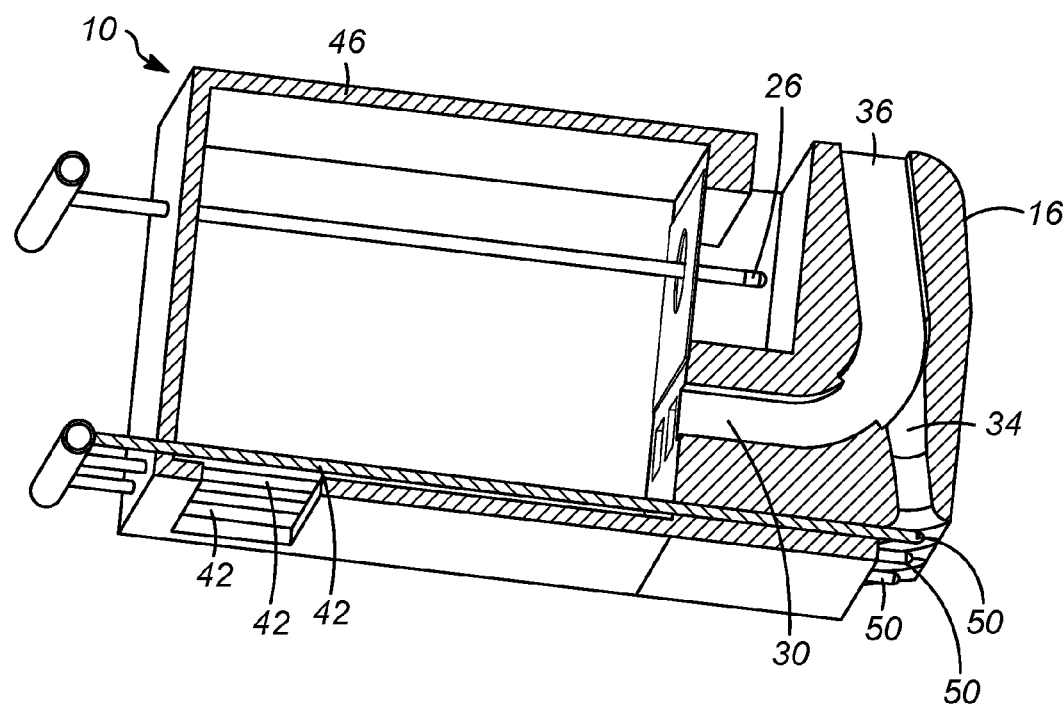
FIG. 5 is a cross sectional view of a second preferred embodiment of a burner assembly constructed according to the present invention.

FIGS. 4 and 5 illustrate a second preferred embodiment of the burner assembly constructed according to the present invention. FIG. 4 is a perspective view of the second preferred embodiment of the burner assembly. The burner assembly sits within a burner tile 16 similar to the burner tile 16 of the aforementioned first preferred embodiment. Primary fuel is injected by primary fuel risers 28 and discharged through primary fuel tips 26. Secondary or staged fuel is injected by staged fuel risers 42. The staged fuel is discharged from staged fuel orifice spuds 50. However, in the second preferred embodiment, the primary fuel is injected by the nozzle mix tip method used in prior art, but the secondary or staged fuel is injected by the improved, premix means.

FIG. 5 is a cross sectional view of the second preferred embodiment of the burner assembly 10. Primary fuel enters primary fuel risers 28 and is discharged through primary fuel tips 26. FIG. 4 shows two nozzle mix primary fuel tips 26, however, the number of tips can vary from a single tip to multiple tips. The primary fuel is injected by the nozzle mix method where combustion air and the primary fuel are only partially mixed prior to the discharge of primary fuel into the combustion zone. The primary fuel is discharged from the primary fuel tips 26 and subsequently enters into the furnace space where combustion takes place.

In the second preferred embodiment, combustion air enters into windbox 46 through windbox openings 44. The combustion air then may enter the burner tile 16 through multiple combustion air inlets 30 that are cast into the burner tile 16 and communicate from the inlet to the furnace space. FIG. 4 shows five combustion air inlets 30, but the assembly can vary from one inlet to multiple inlets. The secondary air inlets 30 create a passageway leading secondary combustion air to venturi channels 34 cast within the burner tile 16. Staged fuel may be injected nearly vertically from the set of staged fuel orifice spuds 50. FIG. 4 shows five staged fuel spuds, but could have anywhere from one to multiple. The staged fuel may consist of natural gas fuel or any other gaseous fuel typically used in industrial applications. The staged fuel orifice spuds 50 are fluidly connected to staged fuel risers 42. The staged fuel from the staged fuel orifice spuds 50 is received by multiple staged fuel venturi channels 34 located above each staged fuel orifice spud 50. Each staged fuel orifice spud 50 corresponds to a staged fuel venturi channel 34. The high velocity staged fuel discharging from the staged fuel orifice spuds 50 entrains combustion products from the furnace space. The staged fuel and entrained combustion products mix within the venturi channels 34. Subsequently, the mixture thoroughly combines with combustion air coming from combustion air inlets 30 before exiting the burner tile 16 through discharge outlets 36 and thereafter enters the burner combustion zone of the furnace.

The discharge outlets 36 are on the top side of the burner tile 16 and are cast into the burner tile 16 with a slight angle so that the mixture of combustion products, staged fuel, and combustion air is injected at a slight angle towards the primary fuel and combustion air mixture which was earlier released in the combustion zone of the furnace. This provides the additional combustion air necessary for the completion of the combustion of the primary fuel. The delayed mixing of the fuel, combustion products, and the combustion air permits more heat transfer to occur during the combustion process which provides for a cooler flame. The low temperature combustion produces low levels of $NO_x$.

Figure 6:
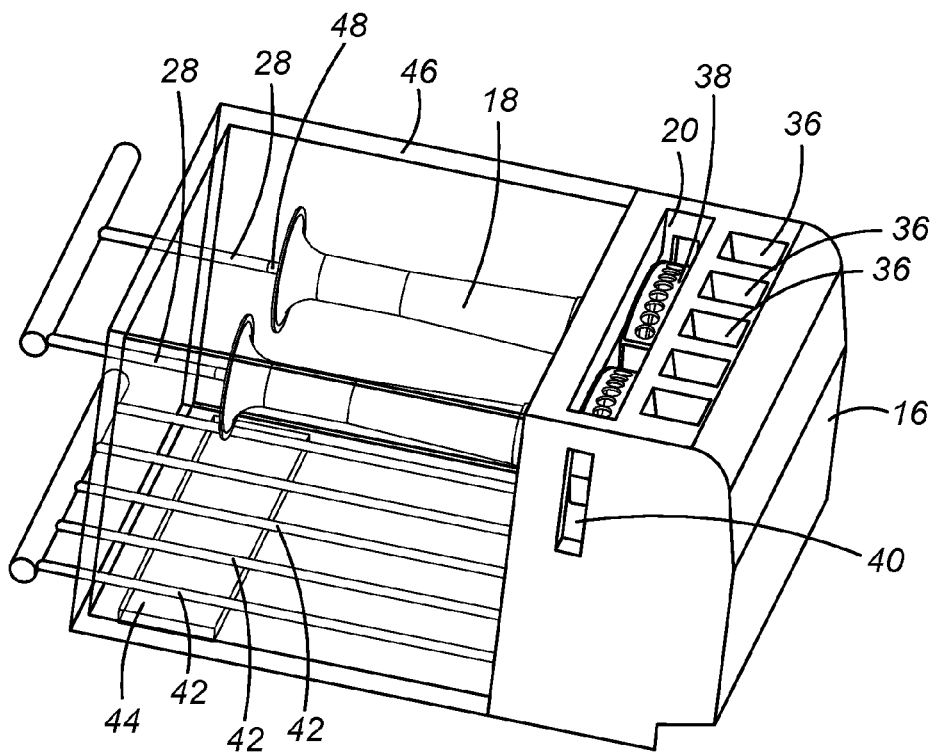
FIG. 6 is a perspective view of a third preferred embodiment of a burner assembly constructed according to the present invention.
Figure 7:
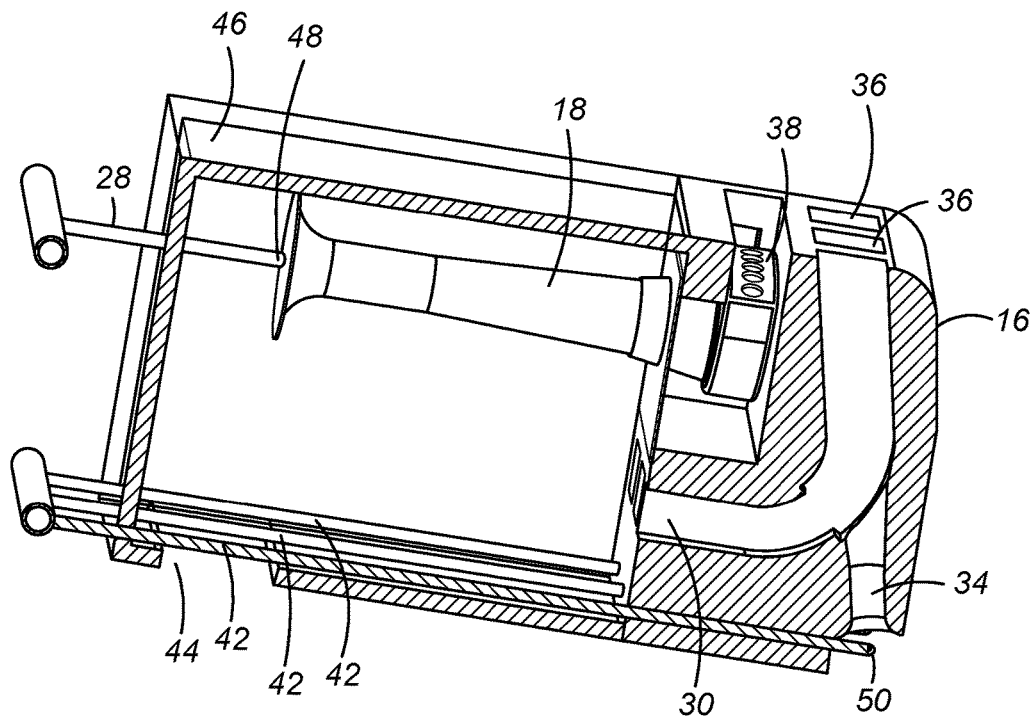
FIG. 7 is a cross sectional view of a third preferred embodiment of a burner assembly constructed according to the present invention.

FIGS. 6 and 7 illustrate a third preferred embodiment of the burner assembly constructed according to the present invention. FIG. 6 is a perspective view of the third preferred embodiment of the burner assembly. The third preferred embodiment discharges both primary fuel and secondary or staged fuel by an improved premix method. Two premix venturi and tip assemblies 18 are shown, but there could be as few as one to as many as multiple assemblies. Primary fuel enters through a primary fuel riser 28 which connects to a primary fuel orifice spud 48 which discharges the primary fuel into the venturi and tip assembly 18. Combustion air coming from outside of the furnace through windbox opening 44 is entrained into the venturi and tip assembly 18 by the primary fuel. Approximately 90% of the stoichiometric air is induced into the premix venturi and tip assemblies 18 and mixes with the primary fuel. A uniform mixture of primary fuel and combustion air exits the premix venturi and tip assemblies 18 through the primary mixer tip 38. The uniform mixture along with entrained combustion products then may exit the burner tile 16 through the burner discharge 20 and may enter into the combustion zone of the furnace. The primary fuel and combustion air mixture that exits the primary mixer tip 38 is a uniform mixture that burns under sub-stoichiometric conditions resulting in low levels of $NO_x$ generation. The fuel and combustion air mixture exits the primary mixer tip 38 at an extremely high velocity. As a result, the high velocity of the primary fuel and combustion air mixture combines with the combustion products in the furnace and adheres to a hot firing wall of the furnace until the mixture reaches the top of the furnace. Due to the high velocity of the mixture relative to the current inside the furnace, the flame is not pulled away from the furnace wall by the low velocity furnace currents. Therefore, the flame does not rollover and contact the tubes. Shown in FIG. 6, the burner tile 16 may have a passageway 40 on either side of the burner tile 16 to allow the high velocity primary fuel and combustion air mixture to circulate combustion products from inside of the furnace into burner tile 16 in order to further reduce flame temperature and subsequently reduce the amount of $NO_x$ generated by the combustion of the primary fuel.

Shown in FIG. 7, combustion air coming from outside of the furnace through windbox openings 44 may enter the burner tile 16 through multiple combustion air inlets 30 that are cast into the burner tile 16 and communicate with the furnace space. The combustion air inlets 30 lead secondary combustion air to venturi channels 34 cast within the burner tile 16. Staged fuel may be injected nearly vertically from the set of staged fuel orifice spuds 50. The burner assembly could have one or multiple staged fuel orifice spuds 50. The staged fuel may consist of natural gas fuel or any other gaseous fuel typically used in industrial applications. The staged fuel orifice spuds 50 are fluidly connected to staged fuel risers 42. The staged fuel from the staged fuel orifice spuds 50 is received by multiple staged fuel venturi channels 34 located above each staged fuel orifice spud 50. Each staged fuel orifice spud 50 corresponds to a staged fuel venturi channel 34. The high velocity staged fuel discharging from the staged fuel orifice spuds 50 entrains combustion products from the furnace space. The staged fuel and entrained combustion products mix within the venturi channels 34. Subsequently, the mixture combines with the combustion air coming from combustion air inlets 30 before exiting the burner tile 16 through discharge outlets 36 and thereafter entering the burner combustion zone of the furnace.

The discharge outlets 36 are cast into the burner tile 16 with a slight angle so that the mixture of combustion products, staged fuel, and combustion air is injected at a slight angle towards the primary fuel and combustion air mixture earlier released in the combustion zone of the furnace. This provides the additional combustion air necessary for the completion of the combustion of the primary fuel. The delayed mixing of the fuel, combustion products, and the combustion air permits more heat transfer to occur during the combustion process which provides for a cooler flame. The low temperature combustion produces low levels of $NO_x$.

Figure 8:
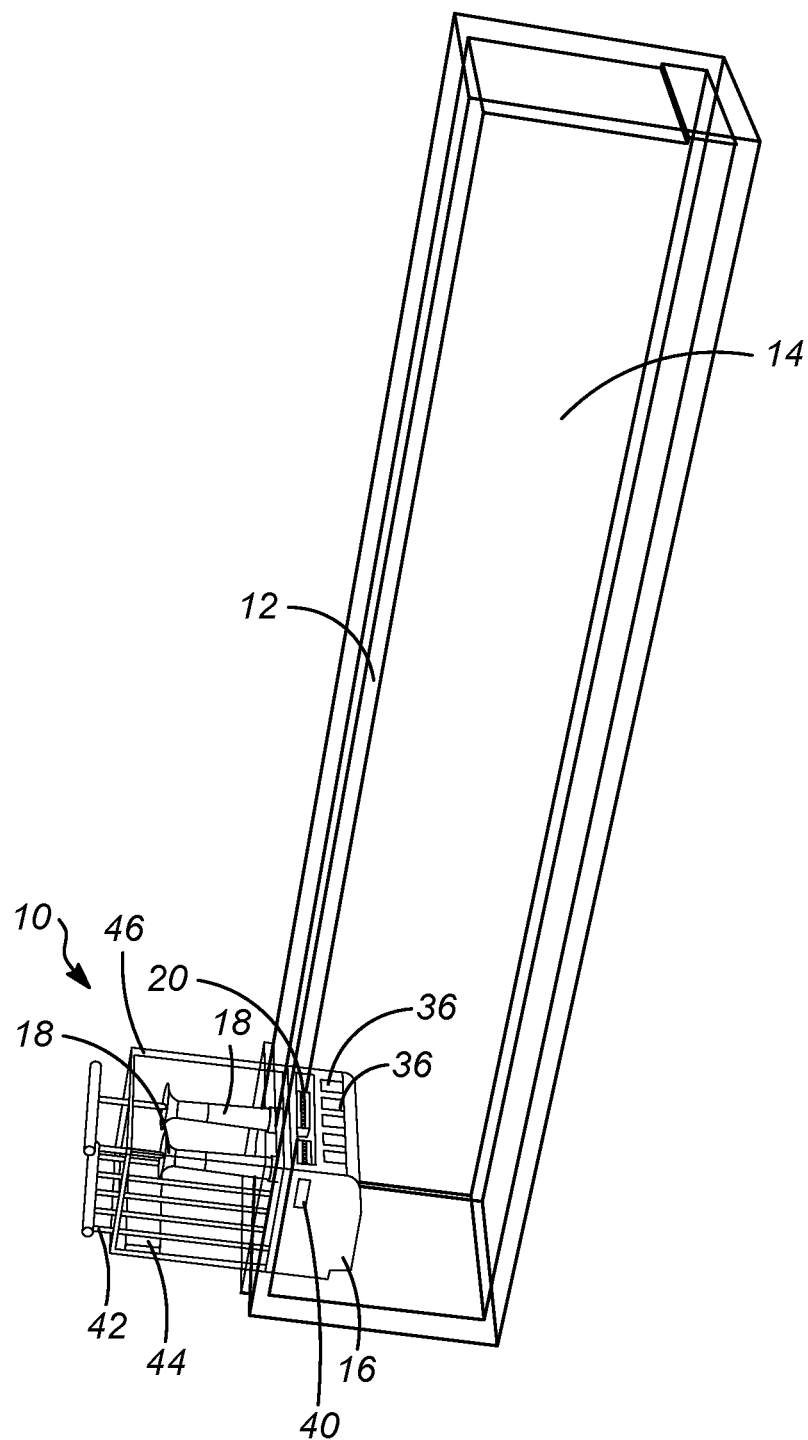
FIG. 8 is a perspective view of a third preferred embodiment of a burner assembly associated with a furnace constructed according to the present invention.

FIG. 8 is a perspective view of an embodiment of a burner assembly where the burner assembly 10 may be adjacent with a wall 12 of a furnace 14. The burner tile 16 of the burner assembly extends into the furnace area and is positioned inside of the furnace. Above the burner tile 16 and still within the confinement of the furnace is referred to herein as the furnace space. A combustion zone is created just above the burner tile, within the furnace space.

The burner assembly 10 includes at least one primary fuel premix venturi and tip 18 and at least one secondary fuel premix venturi assembly (internal to burner tile) cast as part of a burner tile 16.

FIG. 9 is a perspective view of a primary fuel premix venturi and tip assembly 18 standing alone, unattached to the burner tile (not shown). The premix burner assembly 18 includes an inlet 24, a primary fuel orifice spud (internal, not shown), a venturi mixer 22, and a primary mixer tip 38. The primary fuel orifice spud, inlet 24, venturi mixer 22, and primary mixer tip 38 are all in fluid communication with one another.

Whereas, the devices and methods have been described in relation to the drawings and claims, it should be understood that other and further modifications, apart from those shown or suggested herein, may be made within the spirit and scope of this invention.

The invention claimed is:

1. A burner assembly for a furnace, comprising:
   at least one primary fuel tip associated with a burner tile;
   at least one staged fuel orifice spud associated with said burner tile;
   said burner tile including:
      a connective opening for the at least one primary fuel tip;
      a discharge opening to discharge primary fuel in a furnace;
      multiple staged fuel inlets to receive staged fuel from the at least one staged fuel orifice spud;
      multiple angled discharge outlets, wherein said discharge outlets are respectively connected to said staged fuel inlets by way of multiple venturi channels; and
      multiple combustion air inlets to receive combustion air from outside of said furnace, wherein said multiple combustion air inlets fluidly connect to said multiple venturi channels and to said multiple discharge outlets.

2. The burner assembly of claim 1, wherein said multiple discharge outlets release staged fuel, combustion air, and combustion products into a furnace.

3. A burner assembly for a furnace, comprising:
   at least one primary premix venturi and tip assembly associated with and extending outward from a burner tile;
   at least one staged fuel orifice spud associated with said burner tile;
   said burner tile including:
      a connective opening for communication with the at least one venturi and tip assembly;
      a discharge opening for said connective opening;
      multiple staged fuel inlets to receive staged fuel from the at least one staged fuel spud;
      multiple angled discharge outlets, wherein said discharge outlets are respectively connected to said staged fuel inlets by way of multiple venturi channels; and
      multiple combustion air inlets to receive combustion air from outside of said furnace, wherein said multiple combustion air inlets connect to said multiple venturi channels, respectively.

4. The burner assembly of claim 3, wherein said premix venturi and tip assembly comprises:
   an elongated venturi mixing chamber;
   an inlet in fluid communication with said venturi mixing chamber;
   a primary fuel orifice spud for introduction of primary fuel into said inlet;
   a primary fuel riser in fluid communication with a primary fuel orifice spud; and
   a primary mixer tip in fluid communication with said venturi mixing chamber.

5. The burner assembly of claim 4, wherein said primary mixer tip of said premix venturi and tip assembly sits within said burner tile and is positioned such that a primary fuel and combustion air mixture may be released through said discharge opening.

6. The burner assembly of claim 4, wherein said multiple staged fuel inlets of said burner tile receive staged fuel from the at least one staged fuel orifice spud.

7. The burner assembly of claim 4, wherein said multiple angled discharge outlets release staged fuel, combustion air, and combustion products inside a furnace.

8. A method of ethylene production in a furnace with a burner assembly that includes at least one premix venturi and tip assembly, at least one primary fuel orifice spud, at least one staged fuel orifice spud, and a burner tile for combusting fuel in a furnace space, comprising:
   injecting primary fuel through the premix venturi and tip assembly by way of a primary fuel orifice spud;
   inducing approximately ninety percent (90%) of stoichiometric air required for combusting the primary fuel into said premix venturi and tip assembly;
   mixing the primary fuel with said stoichiometric air;
   discharging a uniform mixture of said primary fuel and said stoichiometric air through a primary mixer tip and into said furnace space;
   circulating combustion products from furnace through passageways of burner tile;
   discharging staged fuel into the burner tile through the at least one staged fuel orifice spud wherein the staged fuel leads into multiple venturi channels;
   conducting combustion air through multiple combustion air inlets cast within said burner tile;

inducing combustion products from said furnace and into said multiple venturi channels;

mixing of the combustion products and said staged fuel with combustion air within said burner tile and before exiting said burner tile; and injecting a mixture of the combustion products, the staged fuel, and combustion air at a slight angle towards the uniform, fuel rich mixture of primary fuel and combustion air.

9. The method of claim 8, wherein said uniform, fuel rich mixture of primary fuel and combustion air may burn under sub-stoichiometric conditions resulting in a low generation of $NO_x$.

10. The method of claim 8, wherein combustion of the uniform mixture occurs near to the burner tile.

11. The method of claim 8, wherein said primary fuel and said secondary fuel are both natural gas fuel.

\* \* \* \* \*